United States Patent [19]

Muntwyler

[11] 4,285,971
[45] Aug. 25, 1981

[54] NOVEL HALOGENATED PHENOL ESTERS, ANTIMICROBIAL COMPOSITIONS CONTAINING THEM AND THEIR USE

[75] Inventor: René Muntwyler, Hofstetten, Switzerland

[73] Assignee: Ciba-Geigy Corporation, Ardsley, N.Y.

[21] Appl. No.: 62,192

[22] Filed: Jul. 30, 1979

[30] Foreign Application Priority Data

Aug. 8, 1978 [CH] Switzerland ............ 8473/78

[51] Int. Cl.³ .......... A01N 37/02; A01N 37/06; A01N 37/10; C07C 69/76
[52] U.S. Cl. .................... 424/308; 424/311; 424/312; 424/314; 560/61; 560/65; 560/66; 560/86; 560/105; 560/109; 560/145
[58] Field of Search ............. 424/311, 312, 314, 317, 424/318, 308; 260/398; 560/86, 105, 254, 61, 65, 66, 145

[56] References Cited

U.S. PATENT DOCUMENTS

| 2,508,335 | 5/1950 | Moyle et al. | 424/311 |
| 2,628,249 | 2/1953 | Bruno | 560/254 |
| 3,510,500 | 5/1970 | Walsh | 560/105 |
| 3,669,998 | 6/1972 | Munekata et al. | 424/311 |
| 3,673,237 | 6/1972 | Janlak | 424/301 |
| 3,732,264 | 5/1973 | Baum et al. | 424/312 |
| 3,873,586 | 3/1975 | Henrick | 424/312 |
| 3,926,644 | 12/1975 | Kaye | 424/311 |
| 4,130,659 | 12/1978 | Kijima et al. | 424/312 |

OTHER PUBLICATIONS

J. Sci. Res. Inst. 46, 113-115 (1952)—Sakai et al.
J. Sci. Res. Inst. 48, 38-48 (1954)—Sakai et al.

Primary Examiner—Douglas W. Robinson
Attorney, Agent, or Firm—Edward McC. Roberts; John P. Spitals

[57] ABSTRACT

Halogenated phenol esters of the formula

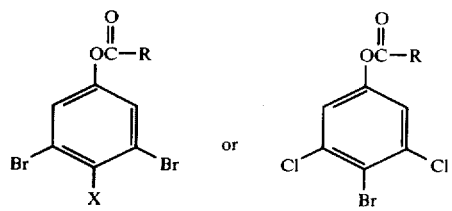

wherein X represents chlorine or fluorine and R represents hydrogen, alkyl of 1 to 22 carbon atoms, alkenyl of 2 to 22 carbon atoms, benzyl which is unsubstituted or substituted by chlorine or bromine atoms, or phenyl which is unsubstituted or substituted by alkyl or alkoxy, each of 1 to 4 carbon atoms, carboxyl, chlorine and/or bromine. The invention also relates to a method of protecting organic and inorganic material from attack by microorganisms, in particular of providing textiles with an antimicrobial and rotproof finish, of protecting wood from rot, and of preventing the formation of slime in the manufacture of paper.

9 Claims, No Drawings

NOVEL HALOGENATED PHENOL ESTERS, ANTIMICROBIAL COMPOSITIONS CONTAINING THEM AND THEIR USE

The present invention relates to novel halogenated phenol esters, antimicrobial compositions which contain them as active component, and a method of protecting organic material from attack by microorganisms, in particular of providing textiles with an antimicrobial, rotproof and mildew-proof finish, of protecting wood from rot and of preventing the formation of slime caused by microorganisms in paper manufacture.

It is known from the Journal of the Scientific Research Institute 46 (1952), 113–117 and 48 (1954), 38–48 (S. Saki et al.) that fatty acid esters of different polychlorophenols, for example of trichloro- and tribromophenols, have a fungistatic action and are suitable in particular for chemotherapy against trichophyton infections. These compounds, however, are unsuitable for the purposes of the present invention, as they either have deficiencies in their activity spectrum, are insufficiently resistant to atmospheric influences, are unsuitable for individual substrates and are difficult to obtain, or for other reasons cannot be used in practice or are of only limited utility.

The present invention is based on the surprising observation that a selected group of trihalophenol esters has an excellent antimicrobial action, that these compounds do not have many of the disadvantages of the known halophenol esters, and that they are therefore most suitable for protecting organic and inorganic material, preferably textiles made from natural fibres, paper making slurries, industrial recirculating water systems, wood, different surfaces etc., from attack by microorganisms, in particular bacteria, algae, and most especially, fungi, and thus also from attack by rot and mildew.

The phenol esters of the present invention have the formulae

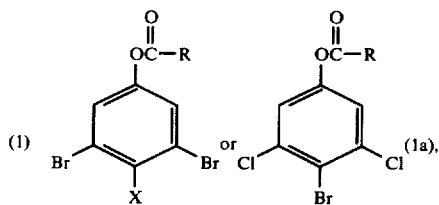

wherein X represents chlorine or fluorine and R represents hydrogen, alkyl of 1 to 22 carbon atoms, alkenyl of 2 to 22 carbon atoms, benzyl which is unsubstituted or substituted by chlorine or bromine atoms, or phenyl which is unsubstituted or substituted by alkyl or alkoxy, each of 1 to 4 carbon atoms, carboxyl, chlorine and/or bromine.

A phenyl radical R can contain 1 to 3 of the substituents named in the above definition. Preferably, however, a phenyl radical R contains only one substituent.

Interesting compounds are those of the formula (1), wherein X represents chlorine, and those of the formula (1a), especially those of the formula (1), wherein X represents chlorine.

Particularly interesting compounds within the scope of the formula (1) or (1a) are those of the formula

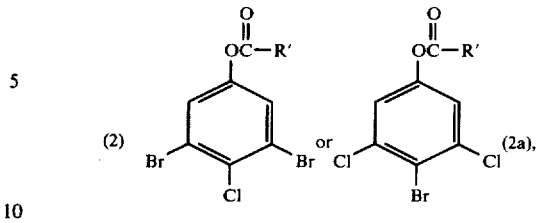

wherein R' represents alkyl of 1 to 22 carbon atoms, alkenyl of 2 to 22 carbon atoms, phenyl or benzyl, especially those of the formula (2).

Preferred compounds within the scope of the formula (1) or (1a) are those of the formula

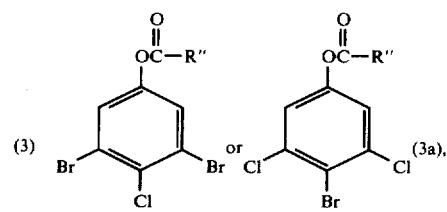

R" represents alkyl of 10 to 22 carbon atoms or alkenyl of 10 to 18 carbon atoms, especially those of the formula (3).

The invention also relates to a method of protecting organic or inorganic material from attack by microorganisms, which comprises incorporating in or applying to the surface of said material one or more of the compounds defined in formulae (1) to (3) or (1a) to (3a).

The present invention also provides antimicrobial compositions which contain a specific amount of one or more of the compounds defined in formulae (1) to (3) or (1a) to (3a). Depending on the end use, these compositions can contain different assistants and solvents. The phenol esters of the invention are readily soluble in organic solvents and in propellant gases for aerosols. The compositions can therefore contain such solvents and propellant gases if it is desired to spray or apply them to surfaces. It will be readily understood that the compounds of the invention can also be dispersed in water or emulsified.

Further assistants which the compositions of the invention may contain are listed in the survey provided hereinafter of the fields of use in which the compounds of the formula (1) or (1a) can be employed. Examples of such assistants are: anionic wetting agents, such as soaps, benzenesulfonates, cationic wetting agents, such as alkylargyl sulfate, nonionic wetting agents, such as polyglycol ethers and higher fatty alcohols, chelating agents, such as sodium hexamethaphosphate, aromatic substances, plasticisers, softeners, fillers, such as silicates, carbonates and/or finishing agents or starch derivatives.

The compounds of the invention can, of course, also be formulated with a solid carrier to e.g. compositions in powder form.

The phenol esters of the present invention possess a broad antimicrobial activity spectrum and exhibit both microbistatic and microbicidal action. Good action is observed against both gram-positive and gram-negative bacteria and algae and, in particular, against fungi. With regard to the technical aspects of their use, the lack of colour and freedom from odour of the compounds are of particular importance.

In accordance with this broad antimicrobial activity spectrum, the phenol esters of the invention can be employed for protecting a great variety of organic and inorganic substrates in a wide field of technology and industry, in particular for preserving and disinfecting industrial products and rendering them resistant to microorganisms and rot. The protection of various materials of organic origin from rot induced by bacteria and fungi is to be singled out for mention. The outstanding action of the compounds employed in the method of the invention against fungi is to particularly highlighted. In this field especially they are superior to the known similar compounds of the prior art. For this reason, it is particularly preferred to employ the phenol esters of the invention in all those fields of use in which an action against a wide variety of fungi is necessary (e.g. protection against rot, mildew etc.). A number of principal fields of use are listed hereinafter.

The compounds of the invention are preferably used for providing fibres and textiles with a preservative and disinfectant finish, and are applied to natural and synthetic, preferably natural, fibres, e.g. cellulose fibres, on which they exert a lasting action against harmful (also pathogenic) microorganisms, e.g. fungi and bacteria. The compounds can be added before, simultaneously with or after a treatment of these textiles with other substances, e.g. colour or printing pastes, flame retardants, fabric softeners and other finishing agents. Textiles thus treated are protected against rot induced by microorganisms.

The formulations in which the compounds of the invention are applied may correspond to those conventionally employed in the art. The compositions used for finishing and protecting textiles should contain the compounds of the invention in a finely divided form. In particular, solutions, dispersions and emulsions of these compounds are therefore used. Aqueous dispersions can be obtained, for example, from pastes or concentrates, and can be applied as liquids or in aerosol form.

The aqueous solutions or dispersions advantageously contain surfactants, for example anionic compounds such as soaps and other carboxylates (e.g. alkali metal salts of higher fatty acids), derivatives of sulforoxyacids (e.g. sodium salt of dodecylbenzenesulfonic acid, water-soluble salts of sulfuric acid monoesters of higher molecular alcohols or of the polyglycol ethers, for example soluble salts of dodecyl alcohol sulfate or of dodecyl alcohol polyglycol ether sulfate), derivatives of phosphorus-oxyacids (e.g. phosphates), derivatives with acid (electrophilic) nitrogen in the hydrophilic group (e.g. disulfine salts), cationic surfactants, such as amines and their salts (e.g. lauryldiethylenetriamine), onium compounds, amine oxides or nonionic surfactants, e.g. polyhydroxy compounds, suffactants based on mono- or polysaccharides, higher molecular acetylene glycols, polyglycol ethers (e.g. polyglycol ethers of higher fatty alcohols, polyglycol ethers of higher molecular alkylated phenols). In addition, the liquor can also contain conventional assistants, for example water-soluble perborates, polyphosphates, carbonates, silicates, fluorescent whitening agents, plasticisers, acid reacting salts, e.g. ammonium- or zincsilicofluoride, or certain organic acids, e.g. oxalic acid, and also finishing agents, e.g. those based on synthetic resin or on starch.

The textiles can be impregnated with the suitable active compounds e.g. by means of hot or cold dyeing, bleaching, chroming or aftertreatment baths, in which connection various textiles finishing processes are suitable, e.g. the pad or exhaust method.

The treatment is expediently carried out in the temperature range between 10° and 100° C., for example between 10° and 70° C., but preferably at about room temperature.

On account of their good solubility in organic solvents, the compounds of the formula (1) or (1a) are also very suitable for application from non-aqueous media. The material to be finished and protected can in this case simply be impregnated with the solutions.

Examples of suitable organic solvents are trichloroethylene, methylene chloride, hydrocarbons, propylene glycol, methoxyethanol, ethoxyethanol and dimethyl formamide, to which may also be added dispersing agents (e.g. emulsifiers, such as sulfated castor oil and fatty alcohol sulfates), and/or other assistants.

Depending on the end use, the content of phenol ester employed as active compound can be, for example, between 0.1 and 50 g, preferably between 1 and 30 g, per liter of treatment liquor.

The active compounds can be used by themselves, or together with other known antimicrobial textile protectants.

Suitable textiles to be finished and preserved are both fabrics of natural origin, such as cellulosic fabrics, e.g. cotton, or polypeptide-containing fabrics, e.g. wool or silk, and fabrics of synthetic origin, such as those based on polyamide, polyacrylonitrile or polyester, as well as blends thereof.

The amount of active compound applied to the textiles is preferably at least 100 ppm, based on the weight of the material.

In general, the textiles are adequately protected against infestation by fungi and bacteria by an amount of 100 to 5000 ppm, preferably 200 to 2000 ppm, of active compound, based on the weight of the material.

Detergents and cleansing agents having excellent antibacterial or antimycotic action are obtained by combining the suitable trihalophenol esters with surface-active substances, especially with active detergents.

The detergents and cleansing agents can be in any desired form, e.g. in liquid, pasty, solid, flake or granular form. The suitable trihalophenol compounds can be incorporated in anionic compounds such as soaps and other carboxylates (e.g. alkali metal salts of higher fatty acids), derivatives of sulfuroxyacids (e.g. sodium salt of dodecylbenzenesulfonic acid, water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), as well as into cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher-molecular acetylene glycols, polyglycol ethers (e.g. polyglycol ethers of higher fatty alcohols, polyglycol ethers of higher-molecular alkylated phenols), or in mixtures of different surfactants. The antimicrobial activity of the halophenol compounds is at the same time completely retained. The content of active compound in the detergents and cleansing agents, based on the weight of these agents, is from 0.1 to 2.0%, generally 0.1 to 3%. Aqueous preparations of such detergents and cleansing agents containing the phenol esters of the invention can be employed e.g. for providing textiles with an antimicrobial finish. They are also suitable as antimicrobial cleansing agents in the food manufacturing and bottling industries, e.g. in breweries, dairies, cheese dairies and slaughterhouses.

The compounds of the formula (1) or (1a) can furthermore be employed for protecting a very wide variety of surfaces from attack by bacteria and fungi. Particular mention in this connection may be made of the treatment of wood (as raw material), articles made from wood, wood shavings, sawdust, leather, hides and pelts. The method of the invention can also be employed for disinfecting and protecting containers for e.g. technical formulations, floors, walls and fittings in stables and slaughterhouses. Depending on the shape of the object to be protected, the above mentioned objects or surfaces are sprayed, coated or impregnated (e.g. wood and leather) with an aqueous or organic solution or dispersion which contains the active compound.

Examples of suitable organic solvents are water-imiscible solvents, in particular petroleum fractions, and also water-miscible solvents such as lower alcohols (e.g. ethanol and methanol), ethylene glycol monomethyl or monoethyl ether.

Preferably, the composition is applied in an amount such that the respective object, after treatment, contains about 0.1 to 10 g/m$^2$ of active compound. In the treatment of wood it is possible, in particular, to prevent or delay the discolouration and rot caused by different fungi during storage.

The compounds of the formula (1) of (1a) and the method of the invention can also be employed in the paper industry, where in particular the formation of slime caused by microorganisms in the machinery used for manufacturing paper is prevented. To this end, the active compound is added either to the pulp or to recirculating water system in the paper factory. The method of the invention can also be employed in analogous manner in other industrial plants where contamination by microorganisms is to be expected. The concentration of active compound will usually be at least 100 ppm, in practice about 100 to 10,000 ppm and preferably 200 to 5000 ppm. When adding active compound to recirculating water systems, a concentration of about 10 ppm often suffices.

A further possible field of use is the preservation of technical formulations, for example: adhesive substances, binding agents, paints, textile assistants and finishing agents, colour pastes and printing pastes, lacquers and similar preparations based on organic and inorganic organic dyes and pigments, also those which contain casein or other organic compounds. Wall and ceiling paints, for example those which contain an albuminous binder, are also protected from attack by pests by the method of the invention. Other uses to be mentioned are: the preservation of water base glues, for example of wallpaper pastes, especially from attack by fungi, the prevention and control of bacteria and fungus infections in animal oils, fats and emulsions, such as cutting oils, boring oils. When preserving paints and lacquers by the method of the invention, the coats and finishes obtained therewith are also protected in particular from attack by fungi. It is also possible to protect plasticisers, permanent sizes (e.g. based on polyvinyl alcohol) or starch sizes. Plastics moulding compounds of all kinds, e.g. derived from polyamides, polycarbonates, polyesters, polyvinyl chloride, polypropionate or polyvinyl alcohol, are also advantageously protected from attack by bacteria and fungi by the method of the invention. When using plasticisers, it is advantageous to add the antimicrobial agent to the moulding compound dissolved or dispersed in the plasticiser. It is expedient to ensure as uniform a distribution in the moulding compounds as possible. The treated moulding compounds can be used to obtain commodities of all kinds in which it is desired to effect an action against bacilli of the most diverse kinds, for example bacteria and fungi, thus, for example, in foot mats, bathroom curtains, seating accomodation, drip channel gratings in swimming, baths and wall hangings. By incorporating the phenol ester of the invention in corresponding wax compositions and floor polishing pastes, there are obtained floor and furniture polishes with disinfectant action.

To bring about the desired effect, the phenol ester is mixed with the above mentioned substrates and formulations and distributed therein as homogeneously as possible. The compound can be employed by itself in the appropriate amount, or dissolved, dispersed or emulsified in a solvent or dispersant which may additionally contain further assistants, e.g. dispersants or emulsifiers. The concentration of active compound should be at least 100 ppm, based on the material to be protected. For practical purpose, the concentration will be about 100 to 10,000, preferably 200 to 5000, ppm.

The phenol esters of the invention can also be combined with other disinfectants and preservatives, when frequently the action is potentiated. Mention may be made in this connection of combinations with other phenol derivatives, aldehydes (e.g. formaldehyde, salicylaldehyde), alcohols, carboxylic acids and derivatives thereof, organometallic compounds (e.g. tributyl tin oxide), halogens and halogen compounds (e.g. chlorine and iodine compounds), carbonic acid derivatives (e.g. dimethyl dicarbonate or diethyl dicarbonate), amines and quaternary ammonium compounds, phosphonium compounds, sulfonium compounds and heterocyclic compounds (e.g. halogenated and/or quaternated pyridine derivatives).

The compounds of the formula (1) and (1a) can be obtained by known esterification methods. Thus 3,5-dibromo-4-chlorophenol, 3,5-dibromo-4-fluorophenol and 3,5-dichloro-4-bromophenol can be reacted with a carboxylic acid of the formula R—COOH, wherein R is as defined in formula (1) or (1a), in an inert solvent and in the presence of a condensation agent. Alternatively, the above phenols can also be reacted, in an inert solvent, with a carboxylic halide of the formula R—COX, wherein R is as defined above and X is chlorine or bromine, in the presence of an acid acceptor, or with a carboxylic acid ester R—COOR$_1$, wherein R as defined above and R$_1$ is alkyl, benzyl or phenyl, accompanied by elimination of the alcohol R$_1$OH. Suitable acid acceptors include tertiary amines, such as trialkylamine and pyridine, hydroxides, oxides, carbonates and bicarbonates of alkali metals and alkaline earth metals, alkali metal alcoholates, such as potassium tert-butylate or sodium methylate. A suitable condensation agent is e.g. dicyclohexylcarbodiimide. The reaction temperature can be in the range between $-10°$ and $+120°$ C., in particular between 20° and 80° C. Suitable solvents and diluents include ethers and ethereal compounds, such as diethyl ether, dipropyl ether, dioxane, dimethoxyethane and tetrahydrofurane; amides, such as N,N-dialkylated carboxy amides; aliphatic, aromatic and halogenated hydrocarbons, especially benzene, toluene, xylene, chloroform and chlorobenzene; nitriles, such as acetonitrile; dimethyl sulfoxide and ketones, such as acetone or methyl ethyl ketone.

The acids of the formula R—COOH and the halides and esters thereof are known or they can be readily obtained by known methods.

3,5-Dibromo-4-chlorophenol and 3,5-dibromo-4-fluorophenol can be obtained by one of the following methods:

(1) By the method described by M. Kohn et al. (Monatshefte der Chemie 47 (1927), 207–240) according to the reaction scheme:

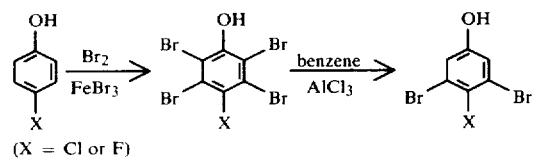

(X = Cl or F)

(2) 1st step as in (1); cathodic debromination by the method of M. Busch et al., Chem. Berichte 70 (1937), 744:

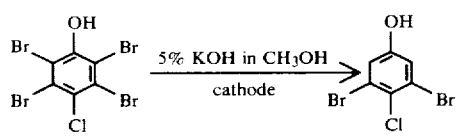

or debromination by the method of H. Hoffman et al., Chem. Berichte 95 (1962), 523:

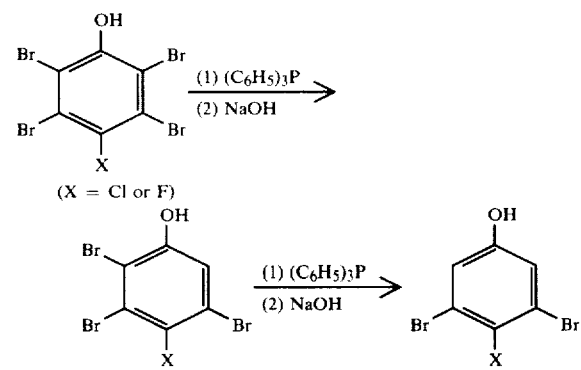

(X = Cl or F)

(3) According to the reaction scheme:

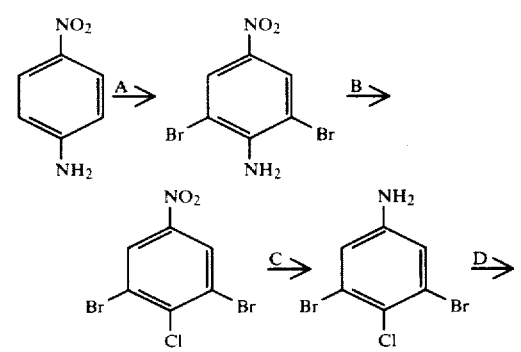

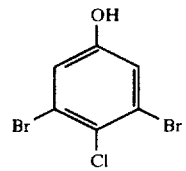

Step A according to Shepherd, J. Org. Chem. 12 (1947), 275, 281, steps B and C according to M. A. F. Hollemann, Rec. trav. chim. 37 (1917), 195, step D according to G. J. Tiessens, Rec. trav. chim. 50 (1931), 112.

(4) 3,5-Dibromo-4-chlorophenol can also be obtained according to the reaction scheme:

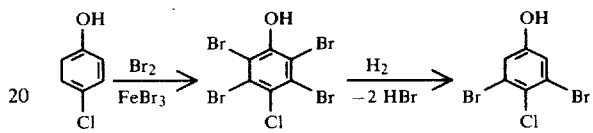

The bromination is carried out conventionally in accordance with e.g. the process mentioned in (1). The debromination is carried out catalytically using a hydrogenation catalyst in an organic solvent and in the presence of a strong base (preferably KOH, NaOH or sodium acetate). An excess of base is employed (preferably about 2 equivalents per equivalent of phenol). A suitable catalyst is preferably Raney nickel, Pd/carbon or Pd/CaCO$_3$. Suitable solvents are alcohols and cyclic ethers (e.g. ethanol, methanol, dioxane). Reference is also made in this connection to H. Kämmerer et al., Chem. Berichte 91 (1958), 1376 and M. Busch et al., Chem. Berichte 49 (1916), 1063.

3,5-Dibromo-4-fluorophenol is mentioned in an article by L. M. Epshtein et al., Bulletin of the Academy of Sciences of the USSR 1975, 2334–9. 3,5-Dichloro-4-bromophenol also used as starting material is mentioned as intermediate by W. S. Gump et al., in J. Soc. Cosmetic Chemists 15, 717 (1964). It can be most advantageously obtained by selective bromination of 3,5-dichlorphenol with bromine. The bromination is carried out in the presence of a Friedel-Craft catalyst, for example in the presence of ZnCl$_2$, AlBr$_3$ or preferably of AlCl$_3$. To increase the selectivity it is possible to use additionally diphenyl sulfide. Preferably the bromination is carried out in the presence of AlCl$_3$ and diphenyl sulfide. An inert, preferably anhydrous organic, e.g. aprotic, solvent, is used as reaction medium. Preferred solvents are anhydrous halogenated aliphatic hydrocarbons, e.g. dichloroethane, methylene chloride, tetrachloroethane, and also anhydrous ethers, such as diethyl ether.

In the following examples, parts and percentages are by weight unless otherwise stated.

EXAMPLE 1

28.6 g of 3,5-dibromo-4-chlorophenol and 7.9 g of pyridine are dissolved in 100 ml of toluene. To this solution is added at room temperature a solution of 21.9 g of lauryl chloride in 30 ml of toluene. The reaction mixture is kept for 2½ hours at 60° C., poured into water and then extracted with toluene. The toluene extract is washed with water, dried and concentrated. The oily residue solidifies in a refrigerator and is then recrystallised from methanol/methylene chloride, affording 40.5 g of the compound of the formula

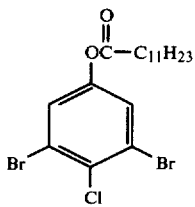

in the form of colourless crystals with a melting point of 41°-42° C.

EXAMPLE 2

The procedure of Example 1 is repeated, using as starting materials 3,5-dibromo-4-chlorophenol, 3,5-dibromo-4-fluorophenol or 3,5-dichloro-4-bromophenol and the corresponding carboxylic acid chloride. The compounds of the formula

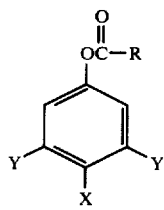

listed in the following table are obtained.

| Compound No. | X | Y | R | m.p. (°C.) |
|---|---|---|---|---|
| 11 | Cl | Br | $C_9H_{19}$ | |
| 12 | Cl | Br | $C_{13}H_{27}$ | 52–53 |
| 13 | Cl | Br | $C_{17}H_{35}$ | 63–64 |
| 14 | Cl | Br | $C_{21}H_{43}$ | 69–72 |
| 15 | Cl | Br | $CH_2=CH-(CH_2)_8$ | colourless oil ($n_D^{20} = 1.5464$) |
| 16 | Cl | Br | $C_{16}H_{33}$ | |
| 17 | Cl | Br | $CH_3(CH_2)_7CH=CH-(CH_2)_7$ | colourless oil ($n_D^{20} = 1.5248$) |
| 18 | Cl | Br | $CH_2C_6H_5$ | 75–76 |
| 19 | Cl | Br | $C_6H_5$ | 130–131 |
| 20 | F | Br | $C_{11}H_{23}$ | |
| 21 | F | Br | $C_{17}H_{35}$ | |
| 22 | Cl | Br | $C_3H_7$ | colourless oil ($n_D^{20} = 1.5732$) |
| 23 | F | Br | $CH_2C_6H_5$ | |
| 24 | Cl | Br | $CH_3$ | 150–152 |
| 25 | Br | Cl | $C_{11}H_{23}$ | 31 |
| 26 | Br | Cl | $C_{15}H_{31}$ | 54–55 |
| 27 | Br | Cl | $C_{21}H_{43}$ | 65–67 |
| 28 | Br | Cl | $C_2H_5$ | 43–45 |
| 29 | Br | Cl | $(CH_2)_7CH=CH(CH_2)_7CH_3$ | colourless oil ($n_D^{20} = 1.5160$) |
| 30 | Br | Cl | ⟨phenyl⟩—Cl | 165–167 |

The trihalophenols used as starting materials can be obtained as follows:

A. (a) 56 g of 4-fluorophenol are dissolved in 400 ml of dichloroethane and 1.5 g of iron powder are added to the solution. The mixture is heated to 60° C. and, with stirring, 352 g of bromine are added dropwise in the course of 1 hour. The temperature is kept for 2 hours at 60° C., then the reaction mixture is cooled to room temperature and poured into water with vigorous stirring. The brown precipitate is collected by suction, washed firstly with dichloroethane and then with water, and dried in vacuo. Recrystallisation from ethanol yields 170 g 2,3,5,6-tetrabromo-4-fluorophenol in the form of brown crystals with a melting point of 178°-180° C.

(b) 83.6 g of 2,3,5,6-tetrabromo-4-fluorophenol are dissolved in 270 g of benzene and, with stirring, 165.5 g of aluminium chloride are added to the solution. The reaction mixture is stirred for 4 hours at reflux temperature, then cooled and poured into ice-water and extracted with toluene. The toluene solution is extracted with 2 N sodium hydroxide, the alkaline aqueous solution is neutralised with acid and extracted once more with toluene. The second toluene extract is washed, dried and concentrated, affording 48.4 g of dark crystals, which are subsequently recrystallised twice from cyclohexane. Yield: 29 g of 3,5-dibromo-4-fluorophenol in the form of brownish crystals with a melting point of 93°-95° C.

3,5-Dibromo-4-chlorophenol with a melting point of 120°-122° C. is obtained by repeating the procedures described in (a) and (b) using 4-chlorophenol as starting material.

B. (a) 128.6 g of 4-chlorophenol are dissolved in 800 ml of dichloroethane. After addition of 1 g of iron powder, the mixture is heated to 60° C. and, with stirring, 704 g of bromine are added dropwise in the course of 1 hour. The temperature is kept for 2 hours at 60° C., whereupon a viscous suspension forms. This suspension is cooled to room temperature and, with vigorous stirring, poured into water. The precipitate is collected by suction, washed firstly with dichloroethane and then with water, and dried. Recrystallisation from alcohol/dioxane affords 380 g of 2,3,5,6-tetrabromo-4-chlorophenol in the form of brown crystals with a melting point of 210°-212° C.

(b) 8.9 g of 2,3,5,6-tetrabromo-4-chlorophenol are dissolved in a mixture of 40 ml of 1 N methanolic KOH and 60 ml of methanol and then 4 g of Raney nickel are added to the solution. Hydrogenation is carried out with hydrogen in a shaking apparatus for 4½ hours under normal pressure at 20° C. The uptake of hydrogen is 98% of theory. The catalyst is removed by filtration and the filtrate is concentrated. The residue is recrystallised twice from cyclohexane, affording 3.5 g of 3,5-dibromo-4-chlorophenol in the form of colourless crystals with a melting point of 121° C.

C. 81.5 g of 3,5-dichlorophenol and 2.5 g of diphenyl sulfide are dissolved in 1 liter of anhydrous ether. Then 2.5 g of anhydrous aluminium chloride are added and 80 g of bromine are added dropwise at room temperature in the course of 10 minutes. The reaction mixture is then stirred for 15 hours at reflux temperature and subsequently poured into water. The organic phase is separated, washed neutral with water, dried and concentrated. The solid residue is recrystallised from cyclohexane, affording 72.6 g of 3,5-dichloro-4-bromophenol in the form of colourless crystals with a melting point of 118°-120° C.

EXAMPLE 3

Test of the bactericidal and fungicidal activity of the phenol esters in the Agar Incorporation Test:

A 5% stock solution of each of the compounds of the formulae (10) to (30) in ethylene glycol monomethyl ether is prepared. A dilution series is prepared from the stock solution, so that the concentration in each individual solution differs by a power of ten. Then 0.3 ml each of the solutions is put into a Petri dish and mixed with 15 ml of hot liquid nutrient medium (nutrient agar). The nutrient medium then contains 1000, 100, 10, 1 and 0.1 ppm respectively of active substance.

After the plates have congealed, the microorganism suspensions are dropped thereon with a Pasteur pipette or with the inoculation device (the microorganisms are the same as those employed in the following Example 4). Bacteria are incubated for 24 hours at 37° C., fungi for 3 days at 28° C. Subsequently, the concentration of active compound up to which the bacilli have grown is determined. All compounds tested exhibit a good bacteriostatic and fungistatic activity against the tested microorganisms.

EXAMPLE 4

Each of the compounds of the formulae (10) to (30) is dissolved in a suitable formulation (ethylene glycol monoethyl ether/dimethyl formamide). The three textile substrates listed below are put into the formulation baths and subsequently squeezed out between 2 aluminium sheets. The substrates are the dried in the air. The squeezing is carried out such that 1000 ppm of active substance are present on the fabric.

1. Reinforced cotton, causticised, bleached, weight per m$^2$: 121 g
2. Polyamide, nylon staple fabric, fixed, bleached, weight per m$^2$: 140 g.
3. Polyester, "Dacron" [Registered Trade Mark] staple fabric, type 54, fixed, bleached, weight per m$^2$: 130 g.

The substrates are then tested against the following 7 test organisms according to the agar diffusion test (modified ATCC test method 90, 1970):

Bacteria
 Staphylococcus aureus ATCC 6538
 Escherichia coli NCTC 8196
 Proteus mirabilis NCTC 8309
 Pseudomonas aeruginosa NCTC 8060
Fungi
 Candida albicans ATCC 10'259
 Trichophyton mentagrophytes ATCC 9533
 Aspergillus niger ATCC 6275

The test plates consist of a twin layer agar, i.e. of a base layer of uninoculated nutrient agar and a surface layer of inoculated nutrient agar.
Bacteria: nutrient agar
Fungi: mycophil agar The filtered micro-organism suspension is poured on a congealed base layer and after the inoculated layer has congealed, discs of the respective substrates of 20 mm diameter are placed on the treated substrates. The bacteria and candida plates are incubated for 24 hours at 37° C.; the fungi plates are incubated for 3 to 5 days at 28° C. After incubation the plates are evaluated for inhibition zones. If there are no inhibition zones, the growth beneath the test samples is examined under a magnifying glass.

The compounds of the formulae (10) to (30) tested in this manner exhibit, in conjunction with the substrates employed, good action against the above bacteria and fungi.

EXAMPLE 5

Crude paper which consists of 90% of bleached sulfite cellulose and 10% of birch is impregnated in a sizing press with a 0.25% solution of the compound of the formula (10) in methanol/water (2:1) to a pick-up of 40%. The dried paper contains 0.1% of active compound, based on its own weight.

To test the action against bacteria, discs of the impregnated paper measuring 10 mm in diameter are laid on brain heart infusion agar plates which have been inoculated beforehand with Staphylococcus aureus. The plates are then incubated for 24 hours at 37° C. To test the action against fungi, paper discs of 25 mm diameter are laid on mycophil agar plates and then inoculated with Aspergillus niger. The plates are then incubated for 72 hours at 30° C. On the one hand, the inhibition zones (IZ in mm) occurring around the paper discs are evaluated, and, on the other, the growth which can be determined microscopically (G in %) beneath or on the discs. The tested compound of the formula (10) exhibits good action against the bacteria employed.

Similar results are obtained using the compounds of the formulae (11) to (30) instead of the compound of the formula (10).

EXAMPLE 6

The following mixture is rolled for 20 minutes at 150° C. on a two roll mill:
 100 g of polyvinyl chloride,
 19.20 g of di-(2-ethylhexylphthalate),
 27 g of di-(2-ethylhexylsebacate),
 1.50 g of Ba/Cd laurate,
 0.25 g of stearic acid
 3.10 g of one of the compounds of the formulae (10) to (30)

The roller nip is adjusted such that 1 mm rough sheets are produced. These sheets are then pressed for 20 minutes at 165° to 170° C. with a pressure of 1400 kg/cm$^2$.

To test the action against bacteria, round pieces measuring 10 mm in diameter are punched from the rolled plasticised polyvinyl chloride and laid on brain heart infusion agar plates which have been inoculated beforehand with Staphylococcus aureus. The plates are then incubated for 24 hours at 37° C. No growth of the test bacteria was observed beneath the discs, regardless of which compound was used.

EXAMPLE 7

A sample of 140 g of cotton/poplin is impregnated at 20° C. for 7 minutes in a bath of the following composition:
 1000 ml of water
 2.7 ml of an after-rinse liquor (containing 7% of a mixture of di-octadecyl- and di-hexadecyldimethylammonium chloride)
 1 g of one of the compounds of the formulae (10) to (30)

The treated fabric is squeezed out to a pick-up of 100% and then dried at 45° C.

To test the action bacteria, discs of the impregnated fabric measuring 25 mm in diameter are laid on brain heart infusion agar plates which have been inoculated with Staphylococcus aureus. The plates are incubated for 24 hours at 37° C. No growth of the test bacteria was observed beneath the disc, regardless of which compound was used.

EXAMPLE 8

An emulsifiable concentrate is prepared by mixing the following constituents:
 10 parts of one of the compounds of the formulae (10) to (30)
 68 parts of xylene 10 parts of dimethyl formamide
12 parts of surfactant.

Before application, the concentrate is diluted with water to 50 to 500 times its volume. Wood, sawdust or cellulose fibres are immersed in the respective emulsion, whereby they are protected against attack by bacteria and fungi.

EXAMPLE 9

An oil-soluble concentrate is prepared by mixing the following constituents:
20 parts of one of the compounds of the formulae (10) to (30)
40 parts of ethylene glycol monoethyl ether
10 parts of dimethyl formamide
30 parts of xylene.

This concentrate is mixed with a paint or cutting oil, such that the paint or oil contains 0,1% of one of the compounds of the formulae (10) to (30) and is thereby protected against bacteria and fungi, regardless of which compound was used.

EXAMPLE 10

A concentrate formulated according to Example 8 is diluted with water to 10 to 100 times its volume and added to the recirculating water in a machine for paper manufacturing, such that the concentration of trihalophenolester is 10 to 200 ppm. The formation of slime that would otherwise occur is effectively inhibited.

EXAMPLE 11

An emulsifiable concentrate formulated according to Example 8 is diluted with water to 200 to 400 times its volume. Rectangular test samples of birch wood measuring 5 cm×5 mm are immersed for 2 minutes in the respective emulsion and dried for 24 hours at room temperature. The samples are then laid on the surface of agar plates. Spore suspensions of *Aspergillus niger* are sprayed onto the plates and the samples. The fungi are incubated for 2 weeks at 95% relative humidity and 28° C. Compared with untreated samples, a pronounced inhibition of the growth of the test microorganisms is observed, regardless of which compound the emulsifiable concentrate contains.

EXAMPLE 12

(a) 8.95 g of one of the compounds of the formulae (10) to (19), (22) and (24) to (30) are dissolved in 120 ml of ethylene glycol monoethyl ether and the solution is stirred into an aqueous mixture which contains 150 g of a water-repellent agent based on a paraffin emulsion containing zirconium salt, and 1.5 ml of 80% acetic acid. The suspension is bulked with water to 1 liter.

(b) 8.95 g of one of the compounds of the formulae (10) to (19), (22) and (24) to (30) are dissolved in 120 ml of ethylene glycol monoethyl ether and the solution is stirred into an aqueous mixture which contains 50 g of a water-repellent agent based on hexamethylolmelamine ether modified with stearic acid and triethanolamine, combined with paraffin, 6.3 ml of acetic acid and 2.5 g of aluminium sulfate (57–60%). The suspension is bulked with water to 1 liter.

Pieces of cotton, cotton/polyester (67/33) and polyacrylonitrile fabric are padded with the suspension obtained in (a) and (b) to a liquor pick-up of 70%, then dried for 10 minutes at 120° C., condensed for 4½ minutes at 150° C. and allowed to condense overnight at room temperature.

After they have been subjected to a spray test and xenon light test, the pieces of fabric undergo a mildew resistance test (DIN 53 931). The bacilli employed are: *Aspergillus niger* ATCC 6275, *Chaetomium globosum* ATCC 6205 and *Penicillium funiculosum* ATCC 9644. Oatmeal-malt agar and mineral salt-cellulose agar are used as nutrient media. The test demonstrates that the tested compounds of the indicated formulae effect a very good mildew-resistant action on the treated fabrics.

What is claimed is:

1. A halogenated phenol ester of the formula

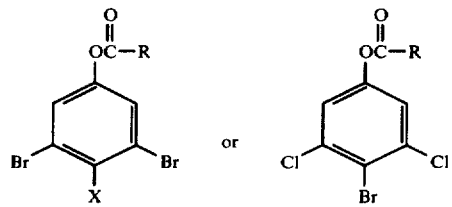

wherein X represents chlorine or fluorine and R represents hydrogen, alkyl of 1 to 22 carbon atoms, alkenyl of 2 to 22 carbon atoms, benzyl which is unsubstituted or substituted by chlorine or bromine atoms, or phenyl which is unsubstituted or substituted by 1 or more substituents selected from the group consisting of alkyl of 1 to 4 carbon atoms, alkoxy of 1 to 4 carbon atoms, carboxyl, chlorine and bromine.

2. A phenol ester according to claim 1 of the formula

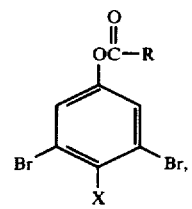

3. A phenol ester according to claim 1 of the formula

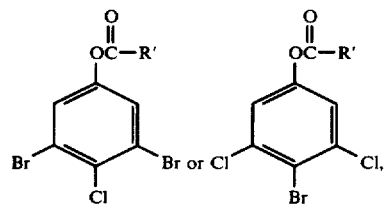

wherein R' represents alkyl of 1 to 22 carbons atoms, alkenyl of 2 to 22 carbon atoms, phenyl or benzyl.

4. A phenol ester according to claim 3 of the formula

5. A phenol ester according to claim 1 of the formula

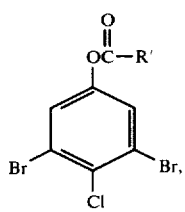

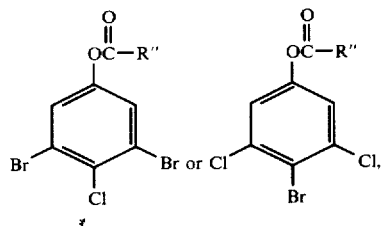

wherein R" represents alkyl of 10 to 22 carbon atoms or alkenyl of 10 to 18 carbon atoms.

6. A phenol ester according to claim 5 of the formula

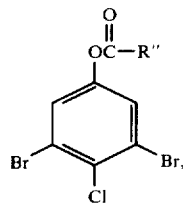

wherein R" represents alkyl of 10 to 22 carbon atoms or alkenyl of 10 to 18 carbon atoms.

7. An antimicrobial composition containing a microbiocidally effective amount of one or more of the phenol esters defined in claim 1 and a carrier therefor.

8. An antimicrobial composition according to claim 7, which contains 0.1 to 20% of phenol ester, based on the total composition, and which additionally contains at least one component selected from the group consisting of water, solvent and conventional excipients, such as wetting agents, chelating agents, aromatic substances, plasticisers, fillers, further antimicrobial compounds and finishing agents.

9. A composition for protecting textiles against attack by microorganisms and against rot and mildew, said composition containing a microbiocidally effective amount of a phenol ester as defined in claim 1, in addition to conventional ingredients of textile dyeing or finishing compositions.

* * * * *